United States Patent [19]

Moore

[11] Patent Number: 4,924,706
[45] Date of Patent: May 15, 1990

[54] METHOD AND APPARATUS FOR DETERMINING RESONANT FREQUENCY OF A TURBINE BLADE MADE OF A METERIAL NOT RESPONSIVE TO A MAGNETIC FIELD

[75] Inventor: Donald W. Moore, Rural Hall, N.C.

[73] Assignee: Westinghouse Electric Corp., Pittsburgh, Pa.

[21] Appl. No.: 334,735

[22] Filed: Apr. 7, 1989

Related U.S. Application Data

[62] Division of Ser. No. 7,100,041, Sep. 23, 1987, abandoned.

[51] Int. Cl.⁵ ............................................. G01N 29/00
[52] U.S. Cl. ..................................................... 73/579
[58] Field of Search ................. 73/579, 583, 651, 652, 73/660, 650, 668, 578

[56] References Cited

U.S. PATENT DOCUMENTS

| | | | |
|---|---|---|---|
| 2,450,939 | 10/1948 | Cor | 73/668 |
| 3,792,348 | 2/1974 | Rollwitz . | |
| 4,002,058 | 1/1977 | Wolfinger | 73/662 |
| 4,026,142 | 5/1977 | Jacobs | 73/578 |
| 4,389,891 | 6/1983 | Fournier | 73/579 |
| 4,482,859 | 11/1984 | Fournier | 324/61 QS |
| 4,682,608 | 7/1987 | De Rigal et al. | 73/579 |

FOREIGN PATENT DOCUMENTS 150549 11/1961 U.S.S.R. ................................. 73/579

Primary Examiner—Hezron E. Williams
Assistant Examiner—Louis M. Arana

[57] ABSTRACT

A method and apparatus for resonant frequency testing of free standing turbine blades made of a material, such as titanium, that is not responsive to a magnetic field is disclosed. A lightweight shim 12 made of a magnetically responsive material such as steel, weighing on the order of 0.5 grams, is attached to the convex side of the blade 10. The shim 12 is excited by an oscillating magnetic field and moves the blade 10 accordingly. The maximum amplitude of blade 10 movement is recorded and used to determine the resonant frequency as the excitation frequency of the magnetic field is swept through a frequency window range. The low weight of the shim 12 does not materially change the resonant frequencies of the blade 10.

13 Claims, 2 Drawing Sheets

METHOD AND APPARATUS FOR DETERMINING RESONANT FREQUENCY OF A TURBINE BLADE MADE OF A METERIAL NOT RESPONSIVE TO A MAGNETIC FIELD

This application is a continuation, of application Ser. No. 07/100,041 filed Sept. 23, 1987, now abandoned.

BACKGROUND OF THE INVENTION

1. Field of the Invention

The present invention is directed to an apparatus and method for exciting a turbine blade made of a material that does not respond to a magnetic field and, more particularly, to a system that attaches a small amount of material that is responsive to a magnetic field to the turbine blade.

2. Description of the Related Art

Free standing turbine blades are replacing the tenoned type blades used in steam generator turbines. Tenoned blades have tips riveted into segments of a ring and several segments are welded together to form a continuous ring. A free standing blade eliminates the need for riveting and welding and makes each blade simpler and less expensive to install. However, a free standing blade behaves like a complex tuning fork and has several modes of resonant vibrations. As a turbine is coming up to speed, it will pass through frequencies that will excite each blade at its resonant frequencies for brief periods. If turbine speed is maintained at one of the excitation frequencies or if a blade has a resonant frequency at or near the normal operating speed, the blade will likely fatigue and fail causing extensive damage to the turbine. As a result, it becomes essential that individual blades be tested to ensure that their resonant frequencies fall within allowable design limits. The measurement of stationary resonant frequency has become a very important measurement. Stationary resonant frequency has been conventionally measured using an accelerometer and mechanical means for exciting the blade. The mechanical exciters were difficult to use and did not produce consistently reproducible results because of adjustment problems.

Recently, a computerized test unit has been built to obtain more accurate stationary frequency test results and to improve the efficiency of the testing process. The computerized frequency test equipment incorporates the use of a non-contact electromagnetic means of exciting the blade and a non-contacting vibration pickup. This non-contact excitation and pickup system improves test repeatability and test efficiency.

This computerized prior art system works well with turbine blades that are made of a material that will respond to a magnetic field but will not work with blades made of a material such as titanium that will not respond to a magnetic field. Since free standing turbine blades are increasingly being made of magnetically unresponsive materials, the need has arisen for a system that will test resonant frequencies of turbine blades made from materials that will not respond to a magnetic field without using a mechanical exciter.

SUMMARY OF INVENTION

It is an object of the present invention to provide a non-contact method for testing turbine blades made of a material that is not responsive to a magnetic field.

It is another object of the present invention to allow non-contact excitation of a turbine blade made of a magnetically unresponsive material without materially changing the resonant frequency of the blade.

It is an additional object of the present invention to provide a device which will aid in the detection of turbine resonant frequencies that does not require contact and will operate with blades made of a material that is not responsive to a magnetic field.

The above objects can be attained by attaching a small amount of a magnetically response material, such as steel, to the turbine blade exciting the material with an oscillating magnetic field and detecting movement of the blade.

These together with other objects and advantages which will be subsequently apparent reside in the details of construction as more fully hereinafter described and claimed, reference being had to the accompanying drawings forming a part hereof, wherein like numerals refer to like parts throughout.

DESCRIPTION OF THE PREFERRED EMBODIMENTS

Figure 1:
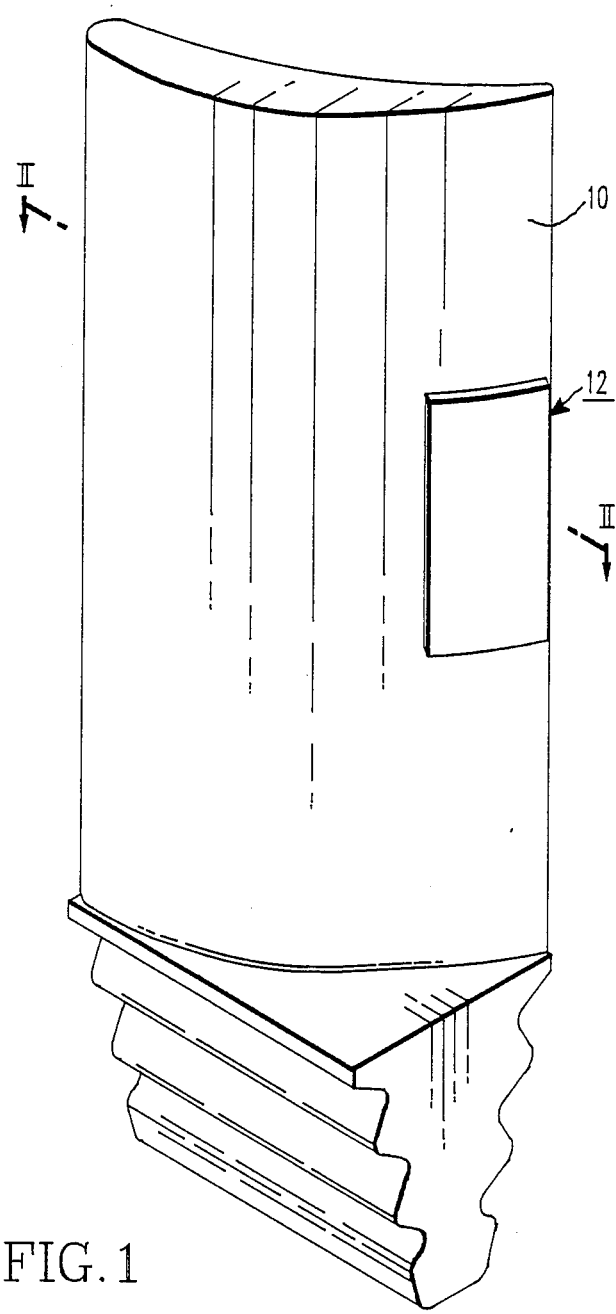
FIG. 1 illustrates a turbine blade 10 with an excitation shim 12 attached thereto in accordance with the present invention.

The present invention excites a turbine blade 10 made of a material, such as titanium, that is not responsive to a magnetic field through an excitation shim 12 attached to the turbine blade 10, as illustrated in FIG. 1. The shim 12 is preferably a steel shim stock material 0.5 inch wide, 3 inches long and 0.002 inch thick. The shim 12 is attached to the blade 0.06 inch from the trailing edge with double faced tape approximately 0.001 inch thick. The shim 12 is preferably positioned approximately two-thirds of the blade length away from the blade base bottom shelf, as illustrated in FIG. 1, which in most blades made by Westinghouse is 10 inches. The shim 12 only adds 0.5 gram of mass to the turbine blade causing a change of approximately 0.1 Hz. in the resonant frequencies of the blade 10.

Figure 2:
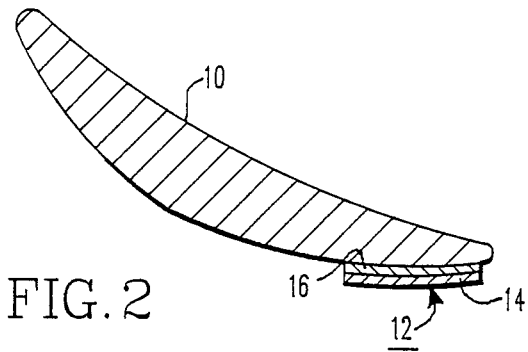
FIG. 2 is a cross-sectional view of the turbine blade 10 of FIG. 1 showing the shim 12 of the present invention in more detail.

FIG. 2 is a cross-section of a blade 10 with a shim 12 attached thereto. As can be seen in FIG. 2, the shim 12 comprises the steel shim stock 14 and a double sided tape 16 such as 3M SCOTCH brand double faced tape core series 2-0300.

The shim 12 is attached to the blade 10 after the blade 10 is mounted in a clamping fixture which holds the blade 10 during testing. During a blade test, a frequency control unit 20 can control the sweeping of the test frequency from 35 Hz. to 1200 Hz. Prior to a test run of a large number of blades, the design engineers have identified the approximate resonant frequencies of the blades and designate one or more windows in which the excitation frequency will be swept. Each window can be as wide as necessary, however, a window of 30 Hz. is preferred to allow rapid testing of each blade. The unit 20 controls the frequency generated by a drive and detection unit 22 which is preferably a resonant frequency test circuit board Model RESFRQ available from Westinghouse. The drive and detection unit 22 sends a frequency test signal to an excitation unit 24 which includes a conventional audio frequency power amplifier and a non-contact magnetic exciter available from the Electro Corporation as Model No. 3010AN. The exciter is mounted on an adjustable stand and positioned approximately ⅜ of an inch from the outlet edge on the convex side of the blade 10 and with a gap of .020 inch between the exciter and the shim 12. The exciter unit 24, through an oscillating magnetic field generated by unit 22 and the shim 12, causes the blade 10 to vibrate. Non-contact proximity sensors available from Kaman Measuring Systems, Model KD2400 are mounted on an adjustable stand. Each sensor is part of a pickup unit 26 which includes an audio band preamplifier for each sensor. One sensor is positioned ⅜ of an inch from the inlet edge on the convex side of the blade 10 and ⅜ of an inch down from the tip of the blade 10. A second sensor is positioned ⅜ of an inch from the outlet edge on the convex side of the blade 10 and ⅜ of an inch down from the tip of the blade 10. Two sensors are used so that twisting of the blade 10 as well as front edge and trailing edge resonances can be detected. A phase detector (not shown) can be attached to the preamplifier for each pickup unit and used to determine whether the blade is being excited in the sixth or seventh harmonics. The amplified response signals are applied to the drive and detection unit 22 which outputs the test frequency and the amplitude of each response signal to a display unit 28 such as a display CRT in a Digital Equipment MicroPDP 11/73 computer. Units 20, 22 and 28 in FIG. 3, along with the phase detector, are available as a complete test set, Model FREME - III from Westinghouse.

Figure 3:
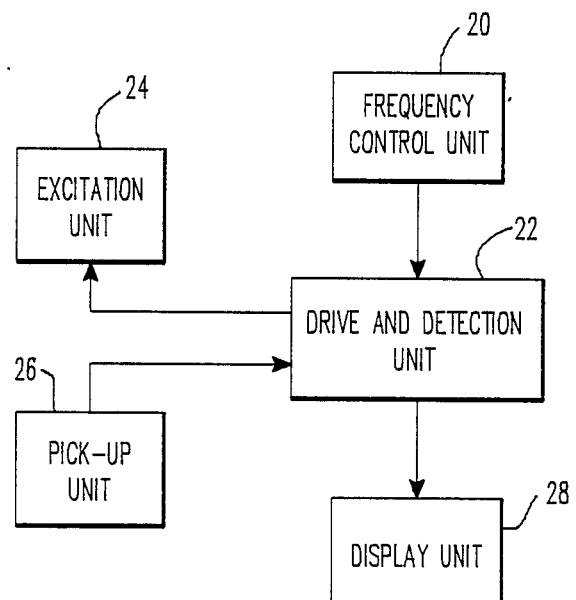
FIG. 3 illustrates an apparatus for exciting the turbine blade 10 through the shim 12 and detecting resonant frequencies.

The apparatus of FIG. 3 is used to determine the resonant frequencies of the blade where a resonant frequency is defined as the frequency of the drive (excitation) signal applied to excitation unit 24 which produces the maximum vibration amplitude under steady state conditions. Because of a dynamic delay, that results in measuring apparent resonant frequencies above or below the actual resonant frequency, as defined above, depending on whether the test drive frequency is swept upward or downward through the measurement window, a bi-directional frequency sweep technique is used. This procedure is a multistep procedure that determines resonant frequency within one of the windows. A first sweep through each window is rapid (approximately 13 Hz./sec.) and begins 5 Hz. below the window and ends 5 Hz. above the window. The apparent resonant frequencies and relative vibration amplitudes for all maximums above a threshold found during this sweep are temporarily stored. The frequency is then jumped back to the apparent resonant frequency with the highest amplitude. This apparent resonant frequency is above the actual resonant frequency so the test drive frequency is now swept downward slowly (at approximately 1.4 Hz./sec.) for a frequency span of 12.5 Hz. and a second apparent resonant frequency and its relative amplitude are determined. The second apparent resonant frequency will be below the actual resonant frequency. From the lower end of this frequency sweep, the system slowly sweeps upward at approximately 1.4 Hz./sec. through a frequency span of 12.5 Hz. and a third apparent resonant frequency is determined together with relative amplitude. The average of the second and third apparent resonant frequencies and their relative amplitudes are calculated and the averages are considered to be the actual resonant frequency and the relative amplitude for this window. If the calculated resonant frequency is outside the window, the next lower amplitude apparent resonant frequency is used as the starting point for a repeat determination of the actual resonant frequency. As soon as a valid resonant frequency is determined for the window, the next window is scanned. As each window is scanned and a valid resonant frequency and relative amplitude are determined, the test results are displayed on the CRT of the computer.

The many features and advantages of the invention are apparent from the detailed specification and, thus, it is intended by the appended claims to cover all such features and advantages of the invention which fall within the true spirit and scope thereof. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

What is claimed is:

1. An apparatus for testing a turbine blade made of a material not responsive to a magnetic field, comprising:
   excitation means for producing a magnetic field;
   means, attached to the blade, for exciting the blade responsive to the magnetic field without substantially changing a natural resonance frequency of the blade and comprising a single steel shim; and
   non-contact means for detecting twisting motion of the blade.

2. An apparatus as recited in claim 1, wherein the blade has a blade base bottom shelf and a length and said single steel shim is attached to the blade approximately two-thirds of the blade length from the blade base bottom shelf.

3. An apparatus as recited in claim 2, wherein said means for exciting further comprises double sided tape between said shim and the blade and changes the natural resonance frequency of the blade less than approximately 0.1 Hz.

4. An excitation and vibration detection device for a turbine blade made of a material not responsive to a magnetic field, comprising:
   means for moving the blade responsive to a magnetic field and changing a natural resonance frequency of the blade less than approximately 0.1 Hz;
   means for attaching said means for moving to the blade; and
   means for detecting twisting motion of the blade.

5. A device as recited in claim 4, wherein said blade has a blade base bottom shelf and a length and said means for moving comprises a single steel shim mounted on the blade approximately two-thirds of the blade length from the blade base bottom shelf.

6. A method of testing a turbine blade having a blade base bottom shelf and a length and made of a material not responsive to a magnetic field, said method comprising the steps of:
   (a) attaching a magnetically responsive material to the blade approximately two-thirds of the blade length from the blade base bottom shelf and having a mass which does not substantially change a natural resonance frequency of the blade;
   (b) exciting the material with a magnetic field; and
   (c) detecting twisting motion of the blade.

7. A method as recited in claim 6, wherein said magnetically responsive material comprises a single steel shim which changes the natural resonance frequency less than approximately 0.1 Hz.

8. An apparatus as recited in claim 1, wherein said non-contact means detects blade edge resonance.

9. An apparatus as recited in claim 8, wherein said non-contact means comprises two proximity sensors held adjacent to front and rear edges of the blade.

10. A device as recited in claim 4, where said detecting means detects blade edge resonance.

11. An apparatus as recited in claim 10, wherein said non-contact means comprises two proximity sensors held adjacent to front and rear edges of the blade.

12. A method as recited in claim 6, wherein step (c) comprises sensing blade edge resonance.

13. A method as recited in claim 12, wherein step (c) comprises sensing front and rear edge motion of the blade.

* * * * *